United States Patent [19]

Lewis et al.

[11] Patent Number: 4,950,271

[45] Date of Patent: Aug. 21, 1990

[54] LIGAMENT GRAFT APPARATUS AND METHOD

[75] Inventors: Jack L. Lewis, Maple Plain; William D. Lew, Mendota Heights; Curtis W. Kowalczyk, St. Paul; Robert E. Hunter, Mendota Heights, all of Minn.

[73] Assignee: Regents of the University of Minnesota, Minneapolis, Minn.

[21] Appl. No.: 307,662

[22] Filed: Feb. 6, 1989

[51] Int. Cl.$^5$ ............................ A61F 2/08; A61F 2/76
[52] U.S. Cl. ........................................ 606/102; 606/99; 623/13
[58] Field of Search ............. 128/92 R, 92 V, 92 VZ, 128/92 VW, 92 VD, 92 VL, 92 VK; 623/13; 606/99, 102

[56] References Cited

U.S. PATENT DOCUMENTS

| | | | |
|---|---|---|---|
| 3,973,277 | 8/1976 | Semple et al. | 623/13 |
| 4,246,660 | 1/1981 | Wevers | 623/13 |
| 4,257,411 | 3/1981 | Cho | 128/92 |
| 4,483,023 | 11/1984 | Hoffman, Jr. et al. | 623/13 |
| 4,597,766 | 7/1986 | Hilal et al. | 623/13 |
| 4,739,751 | 5/1988 | Sapega et al. | 128/92 |
| 4,834,752 | 5/1989 | Van Kampen | 623/13 |

OTHER PUBLICATIONS

Journal of Bone and Joint Surgery by Robert C. More, M.D. et al., Aug. 1978, Article entitled "Measurement of Stability of the Knee and Ligament Force after Implantation of a Synthetic Anterior Cruciate Ligament", pp. 1020–1031.

Primary Examiner—Robert A. Hafer
Assistant Examiner—Kevin G. Rooney
Attorney, Agent, or Firm—Kinney & Lange

[57] ABSTRACT

A knee reconstruction apparatus and method provides for controlling and adjusting the point of fixation of a ligament graft, for example a replacement for the anterior cruciate ligament, which permits precisely and repeatably adjusting the length of the ligament graft or graft components with the joint under a prescribed load prior to fixation. A fixture is fixed on the tibia and includes an adjustable clamp that holds a ligament graft anchored or held in the femur. The clamp can be moved for adjusting the length of the ligament graft, or individual segments of a composite ligament graft while the joint is under a prescribed load. The load carried by one or more individual graft components also can be measured prior to fixation to ensure that each of the segments of a composite ligament graft will carry the desired or selected load for a joint under a prescribed load.

15 Claims, 5 Drawing Sheets

LIGAMENT GRAFT APPARATUS AND METHOD

This invention was supported by the NATIONAL INSTITUTES OF HEALTH, under Grant No. AR38398. The U.S. Government has certain rights to this invention.

BACKGROUND OF THE INVENTION

1. Field of the Invention

The present invention relates to apparatus and methods for repairing ligament damage in a joint by providing a ligament graft member with proper position and fixation.

2. Description of Prior Art

In prior art, various methods of repairing damaged ligaments and joints, such as the anterior cruciate ligament (ACL) in a knee, have been advanced, including installing ligament graft members such as artificial ligaments. These ligament grafts may be portions of tendons that have been taken from other parts of the body. The ligament grafts are generally fixed in tunnels in or to the surfaces of the two bone parts or segments forming the joint by fixation screws, sutures, staples or other securing means. The problem has been that such ligaments will tend to loosen or rupture when exposed to joint motion during daily activities. The tunnel exit hole or port locations or other fixation points in the femur and on the tibia for such ligament graft members have been provided with the graft member then across between the interface of the two bone sections forming the joint. The graft members are anchored to the bone sections, and it has been known to preload such ligament grafts before they are fixed into position. However, it is desired that the length of and the loading on such ligament grafts does not change substantially during the range of motion of the joint and obtaining the desired positioning of the effective attachment site, and the length of such ligaments has been a drawback in any reconstructive surgery. Reproducibility of such reconstruction also remains an elusive goal.

Prior art efforts have concentrated on precisely locating the openings for the tunnels for such grafts and the attachment sites to overcome the problem of excessive shortening and lengthening experienced by the replacement ligament graft. Attempts to precisely locate such ligaments through the use of apparatus that locates the bone tunnels accurately has been explained and reviewed in U.S. Pat. No. 4,739,751. It is explained in that patent that some change occurs in the natural ACL as the knee joint flexes, but many surgeons seek an "isometric" relation of ligament grafts which means no change in attachment site distance as the tibia and femur flex.

A surgical drill guide for making tunnels for ligament grafts is also shown in U.S. Pat. No. 4,257,411. However, while proper location of the tunnels is a concern, it is generally believed that accurately and evenly loading segments or strands of reconstructive ligaments, whether artificial or natural and thus controlling the length, as well as accurately placing the attachment site leads to more reliable rehabilitation and repair of injured joints.

SUMMARY OF THE INVENTION

The present invention relates to an apparatus for positively adjusting the length and thus determining the amount of force being carried by a ligament graft with the knee under external load, and in particular permitting one to provide a multiple strand or segment ligament graft and to prescribe the load shared between the segments. Adjusting the length of the ligament graft segments and accurately locating the attachment sites at the respective bones forming the joint aids in proper reconstruction.

The apparatus utilized includes a frame which mounts on one of the bone portions, for example on the tibia, adjacent to a joint, such as the knee joint, and which receives ligament graft members that have been anchored in the other bone portion adjacent the joint so that the length of the members can be precisely adjusted to exert a desired force or tension on each of the graft components with the knee loaded under an external standard, selected load, prior to fixation.

The external load to be applied to the joint prior to fixation is a load selected to be a proper amount for strength of the graft when healed. The load might be set at different levels for different applications. One way to do the load setting is to approximate the load on a normal ligament which can be determined by laboratory testing.

Additionally, as has been treated in the prior art, the point of effective attachment site of a ligament at the joint interface on the bone segment or portion can affect the flexing of the joint, so that apparatus is provided for adjusting the position of the fixation site of a ligament graft to permit not only adjusting the length of the ligament graft but also arriving at a location where the change in loading is minimized between the ligament graft and the original ligament before injury, and joint operation is maximized or enhanced.

DETAILED DESCRIPTION OF THE PREFERRED EMBODIMENTS

Figure 1:
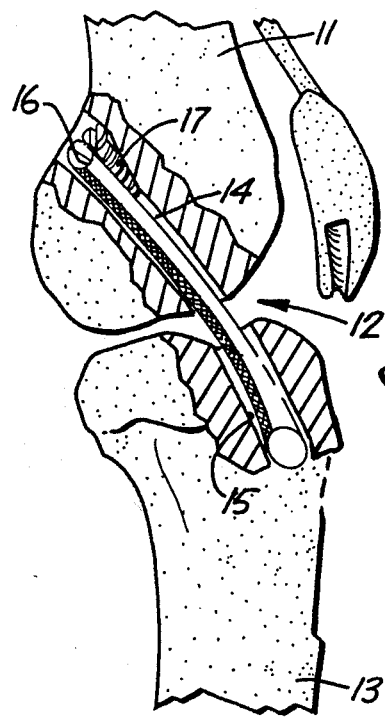
FIG. 1 is a schematic view of typical ligament graft installed in a knee joint, and showing one end anchored in place in a femur and the other passing through a tunnel in a tibia, and used for purposes of illustration and explanation.

FIG. 1 illustrates schematically a typical ligament graft member in a knee joint, for purposes of background information. The repair shown in FIG. 1 schematically is for an anterior cruciate ligament (ACL) which is one of the most commonly and totally disrupted of the knee ligaments. The ACL is partially or completely torn over 70% of the time when there has been substantial trauma causing ligament damage in a knee. If left untreated the ACL ruptures lead to increased anterior and rotary instabilities and meniscal tears, and in many patients joint space narrowing and osteoarthritis. In FIG. 1, a composite graft is shown, and by way of illustration the femur indicated at 10 and the tibia 13 meet at the knee joint indicated at 12. In replacement of the ACL, tunnels or bores are formed, which open to the interface surface of the joint and which have openings or ports defining the attachment site of the ligament graft. In the femur the attachment site is toward the rear of the intercondylar notch, but only a schematic showing is made. A tunnel or bore 14 is formed in the femur which is of size to receive the ligament graft and permit fixing it to the wall of the tunnel to the outside wall of the femur. Preferably the tunnel will exit at substantially the point of attachment of the actual ACL. A second tunnel 15 is formed in the end of the tibia forwardly of the tunnel in the femur to closely simulate the attachment site of the ACL. A ligament graft member indicated generally at 16 is then used to replace the ACL and it is passed through the tunnel in the femur and is held in place with a bone fixation screw indicated at 17 or some other means of anchoring the ligament graft in place. The opposite end of the ligament graft 16 passes into the tunnel 15. With a standardized external load applied to the joint (the knee), the positioning and length of the ligament graft can be adjusted, using the present apparatus to closely match the conditions in a normal ligament. The free end of the ligament graft 16 is fixed in place and the surgery is completed by closing the wound. As shown, sutures 18 can be used for holding graft segments together and for adjustment of ligament length.

Ligament grafts may be made of single or composite grafts, as is commonly known in the field.

Synthetic materials that are used include carbon fibers coated with polylactic acid, high strength Dacron polyester fiber, woven polypropylene, or Gortex material made by W. L. Gore Company. The synthetic material may be used as an ACL prosthesis or to augment and protect a biological segment of a graft. In some instances, a patellar tendon can be segmented from the petella and the tibia, along with end portions of bone, and used as part of the ligament graft. If it is augmented with synthetic materials the sections can be sutured together, or as will be shown the segments or strands can be maintained separately for length adjustment and then fixed as a unit in the tunnel in the tibia.

Preferably, the ligament graft is positioned in the tunnels so that its length, that is the distance between its attachment points or sites, will not significantly change as the knee is fixed through a normal range of pivoting motion.

In the prior art, the isometric position of the ligament graft is located using a device called an isometer. Suture material or thread is commonly placed through a small pilot hole and is fixed to either the outside of the tibia or to the femur at one end and is connected to an isometer at the other end. With the suture under a constant spring load supplied by the isometer the knee is carried through a range of passive flexion/extension, with the isometer indicating the resulting length change of the suture. The pilot hole is then relocated until any length during flexion/extension is within an acceptable limit. These pilot holes then are used for the center of the fixation tunnels, and once the fixation tunnels as generally shown in FIG. 1 are drilled through the bone the ligament graft is placed within the tunnels and is fixed to the tibia and the femur.

Fixation is achieved by using sutures, staples, screws and washers, or a combination of these. For purposes of this application, the fixation devices are prior devices that fix the ligament graft in position, once the appropriate locations and the proper length and loading has been achieved through the use of the present apparatus, and following the method described herein.

Typically, after having fixed the graft to the bone at one part of the joint (a first bone portion) the knee is held at a flexion angle generally in the range of 30°, and then a certain level of external load is applied to the joint while fixation is achieved at the other end of the ligament graft. The joint can be in some other chosen state.

It has been found that the mechanical state of the prior art reconstructed joints was not reproducible from knee to knee, nor did the mechanics of the reconstructed joint match a normal knee. Two probable sources of this variability were the graft attachment site location, and the length of the graft at the time of fixation. At every flexion angle, the knee has a lax region where the articular surfaces can passively displace and rotate over each other until a ligamentous, capsular, or bony constraint is met. This lax region is much larger in an injured knee. Depending upon how the external load is applied prior to the final graft fixation, the articular surfaces will displace relative to each other so that the configuration of the joint and the subsequent length of the graft (as a function of external load) at the time of fixation will vary causing the lack of reproducibility that has been noted.

The mechanical state of the knee during graft fixation can be controlled with the present apparatus, and following the present method, so that the graft length and the attachment site are varied with the knee joint under external load such that the force in the ligament graft matches that which the normal ACL would experience in a similar situation.

Figure 2:
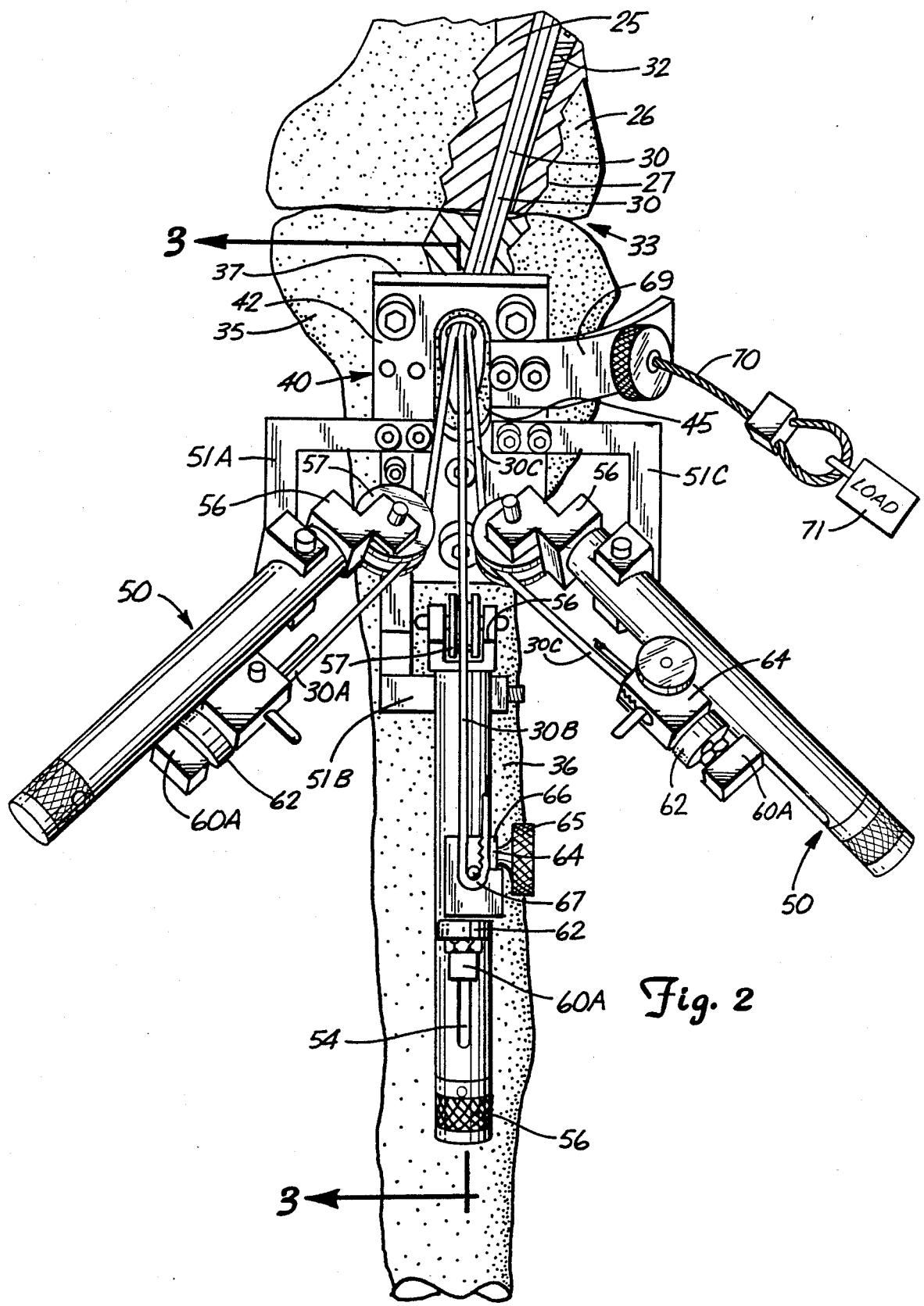
FIG. 2 is a top view of an apparatus used for permitting length and load adjustments in a ligament graft.
Figure 3:
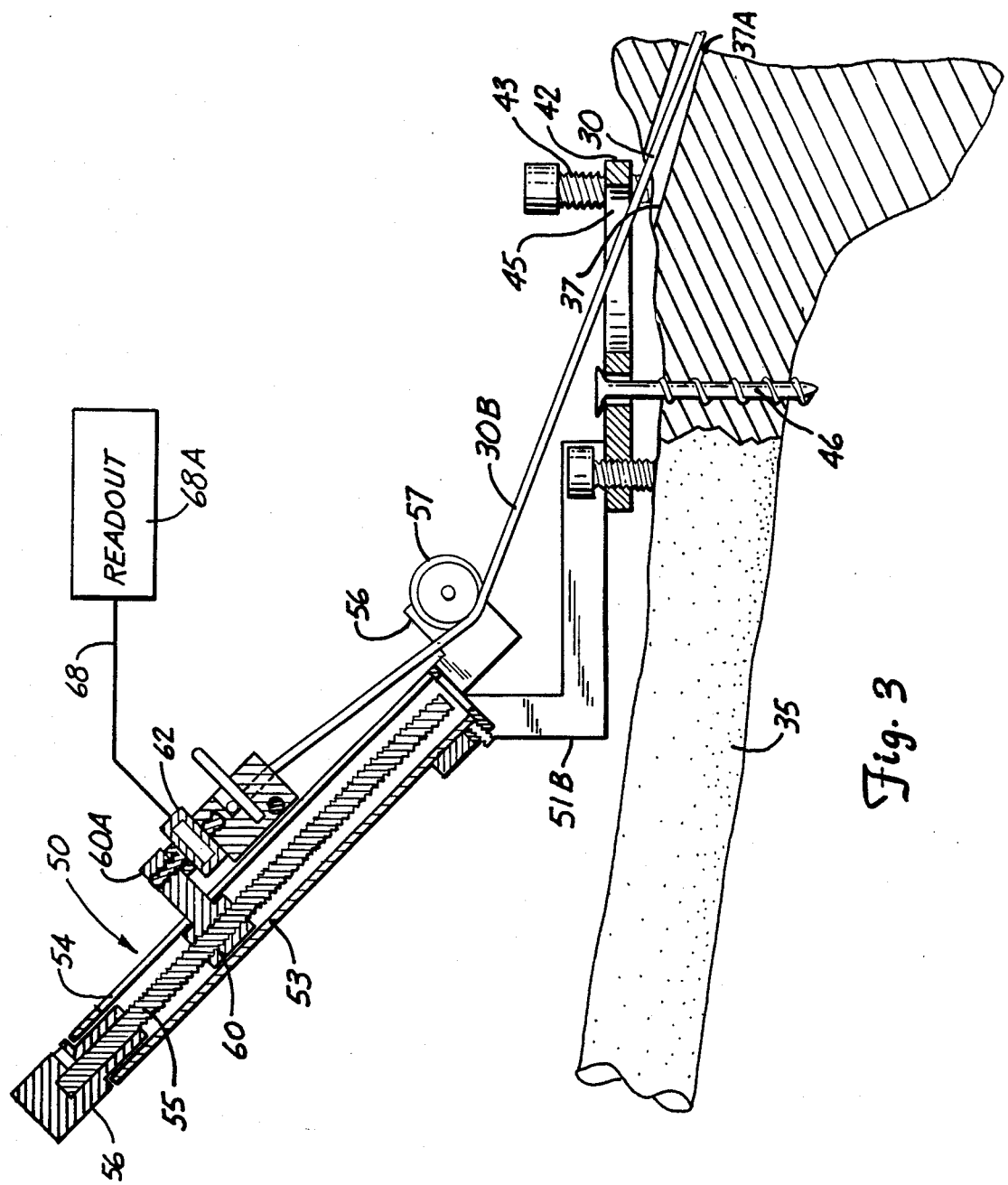
FIG. 3 is a section view taken generally along line 3—3 in FIG. 2.
Figure 4:
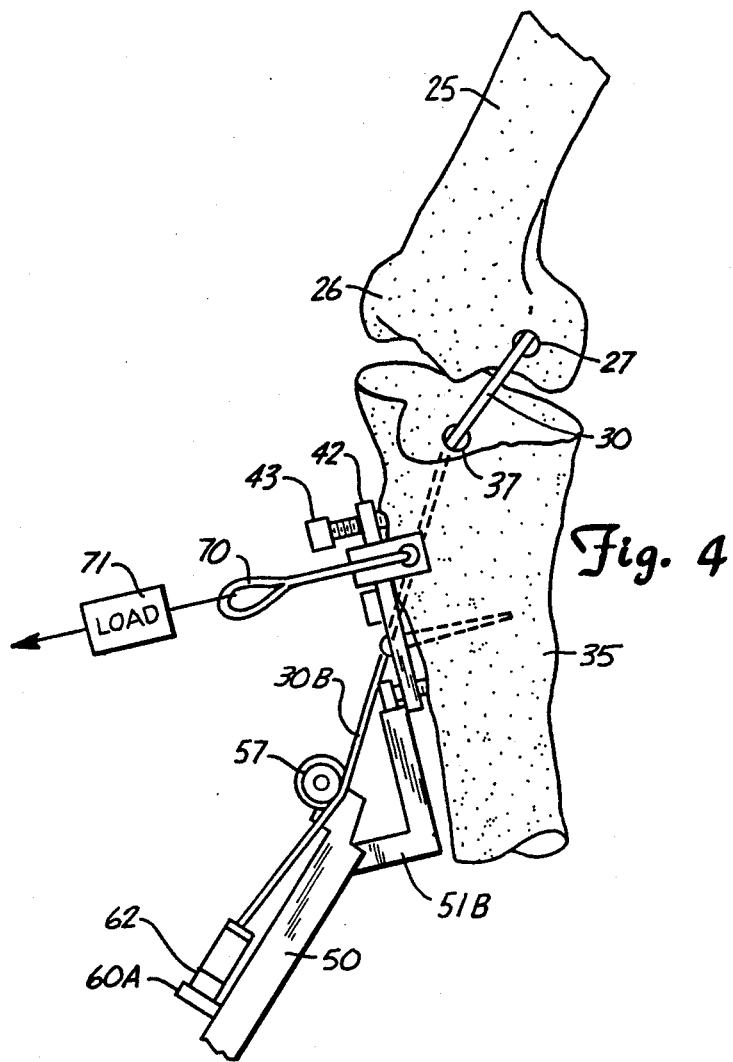
FIG. 4 is a side elevational view of a knee joint illustrating schematically the application of an external load to the knee joint at the same time the apparatus shown in FIG. 2 is being used to adjust the graft length.

Referring to FIGS. 2 and 3 in particular, and also FIG. 4, a device for determining the ligament graft length of individual components of a composite graft, or of a single graft is shown. Assuming that the tunnels in the femur and tibia are properly located, which can be done with the device of FIGS. 5 and 6, an illustration of the present graft loading apparatus shows the femur indicated generally at 25 has a femoral knee joint end 26 (formed of inner and outer condyles), and a tunnel 27 has been located in a proper location for the ligament graft. A ligament graft, which is a polystrand or composite segment ligament graft indicated at 30 is fixed in the femoral tunnel in a suitable matter such as using a bone screw 32 in the tunnel 27 so that one end is fixed at a reference position that can be selected in accordance with the surgeon's needs. The bone screw 32 will force the ligament graft against side surfaces of the tunnel, and the ligament graft then will span the interface indicated at 33 between the knee joint end 26 of femur and the knee joint end 35 on the tibia shown generally at 36. A tunnel 37 in the tibia has an opening or port 37A at the interface surface that is shown in FIG. 3, and a fixture indicated generally at 40 is mounted on the tibia and is used for setting the length of the individual components or graft segments shown at 30A, 30B and 30C of the ligament graft. The port or opening 27A of tunnel 27 at the joint interface and port 37A are spaced apart and the length of ligament graft between these ports when the ligament graft is fixed in position is important.

The individual components or segments can be sutured together adjacent the fixation screw 32 if desired so that they are held as a unit, but the individual segments or strands are used separately in the form shown in FIG. 2 utilizing fixture 40. The tunnel 37 also opens to the exterior of the tibia and the fixture 40 is positioned adjacent the outlet of tunnel 37.

As shown in FIGS. 2 and 3, the fixture 40 has a mounting or base plate 42 that is supported onto the medial tibial flare, over the exit port or opening of the tunnel 37. The plate 42 is spaced from the surface of the tibia utilizing adjustment or leveling screws 43 that are threaded through the plate 42 and have ends which bear against the outer surface of the tibia to provide the desired spacing. The plate 42 has an exit opening 45 of suitable size that overlies the opening or exit port from the tunnel 37. The plate 42 is held against the tibia, and bearing pressure is placed on the support screws 43 through the use of a bone screw 46 that is threaded into the bone and tightly holds the plate 42 in position.

The plate 42 forms a base that can be used for exerting external loads on the joint as well as supporting graft length adjusting assemblies. The plate 42 supports three individual ligament graft segment length adjusting assemblies 50. Each of the length adjusting assemblies is substantially identical in construction, and will be identically numbered, but they are mounted on different brackets and at different locations on plate 42 (see FIG. 3). Each length adjusting assembly 50 includes a device for measuring of loads on the ligament graft segment being adjusted in length. The length adjusting assembly 50 for the graft segment 30B is mounted on a bracket 51B that centers the axis of the length adjusting assembly 50 along the central axis of the tunnel 37, while the length adjusting assembly 50 for changing length and measuring the force on the ligament graft segment 30A is mounted on a bracket 51A that is attached to the plate 42 and extends laterally therefrom so that the segment 30A is directed to the side of the tibia. As can be seen the length adjusting assembly 50 has a guide roller for properly guiding the ligament segment 30A. The length adjusting assembly 50 for the graft segment 30C is mounted on a bracket 51C that is to the other side of the plate 42 and tibia from the bracket 51A so that there is clearance from the center length adjusting assembly 50.

Each of the length adjusting assemblies 50 is constructed as shown generally in FIG. 3, and includes an outer sleeve or tube 53 which has an elongated slot 54 on one side thereof. A screw 55 is rotatably mounted on the interior of the tube 53, and a nut 56 is fixed to one end of the screw 55 and positioned outside the tube at an outer end to support and carry the loads on the screw 55 against the end of the tube 53.

At the inner ends of the length adjusting assemblies 50 there are brackets 56 mounted that in turn rotatably mount graft segment guide pulleys 57. The guide pulleys 57 rotate about axes that are oriented to properly guide the individual ligament graft segments, and prevent binding of these segments as the length is adjusted.

A traveling nut 60 is threadably mounted on each of the screws 55, and has a projection portion 60A that extends through the slot 54 of each of the respective tubes 53. The projection 60A is connected to a load cell 62 and clamp 63. The load cell 62 is shown only schematically and is of suitable design. The load cell 62 can be attached to the projection 60A through the use of an attachment screw or with adhesives. Load cell 62 can be a strain gauge type device that has the ability to measure the level of forces that are carried by the graft segments as the lengths are adjusted. A clamp 64 is connected to the outer end of the load cell in a suitable manner and is used for clamping the free ends of a ligament graft segment. The clamps 64 have a threaded screw 65 that can release a clamp jaw block 66 and clamp the graft segment to the main clamp body after the graft segment has been passed around a post 67.

The load cell 62 can be a conventional purchased load cell unit of known design, so that it would have an output line 68 leading to readout equipment indicated by the block 68A that could read out individually the amount of tension load generated in the ligament graft segment. The pulleys 37 have shallow peripheral grooves for guiding the respective ligament graft segments, and they are made so that they freely rotate to avoid applying loads to the ligament segments or binding as the ligament segments are adjusted in length.

The length adjusting assembly 50 that is used with the ligament graft segment 30A, as shown, is held by its bracket 51 so that the axis of rotation of the guide pulley 57 is substantially upright, and it can be seen that the tube inclines at a desired angle away from the tibia so that it has clearance for operation as the ligament graft segment 30A is adjusted in length. The pulley 57 is positioned to guide the ligament graft segment in a substantially straight path through the tunnel 37 and to the clamp used. The length adjusting assembly 50 used with the ligament graft segment 30C likewise is inclined in its bracket 51C and the pulley 57 properly guides the ligament graft segment 30C. Each of the length adjusting assemblies 50 has an individual load cell 62 that will provide an output load reading.

When the ligament graft has been anchored with the screw 32 in the femur, and the ligament graft segments 30A, 30B and 30C have been clamped in their respective clamps 63 by moving the clamp block 64, the individual ligament graft segments are adjusted so that they are at the desired length by adjusting the traveling nut 60 along the length of the respective screw 55. The nuts 60 are at desired locations so that the necessary length adjustment is possible. Then the knee is flexed so that the tibia forms generally in the range of a 30° angle relative to the femur, as shown in FIG. 4. The plate 42 has a loading bracket 69 thereon that is provided with a loading cable 70, and a suitable scale or load indicating means 71 that can be manually pulled, but which will measure the applied load is connected to the cable 70. A standardized force will be applied to the flexed knee in a direction selected as desired but tending to pull the tibia away from the femur to produce a load in the individual ligament graft segments. This external load is selected to be a load sufficient to provide a good graft and may be the same as the force carried by a normal ligament which is being replaced. The normal force can be determined by laboratory testing. As shown, the external load placed on the joint through cable 70 will be substantially the same as the load in a normal ACL.

Ligament segment length adjustments can be made by threading the screws 55 to prevent the knee interface indicated at 33 from separating and to keep the joint components properly located. When the external joint load desired has been registered on the load indicating means 71, the lengths of the individual ligament graft segments are adjusted until the individual loads indicated by each of the individual load cells 62 are at a desired relationship to each other. The ligament graft segments 30A, 30B and 30C may be adjusted in length to equally share the load or the individual loads may be set at unequal but clinically desirable levels. Once the desired load arrangement has been reached, the individual graft segments then can be fixed or secured as a unitary ligament graft to the sides of tunnel 37. A temporary type fixation can be made and the knee joint flexed to make sure that it is working properly. Once the permanent fixation is done, the plate 42 can be removed. If the knee is flexed before the ligament graft is secured in tunnel 37, changes in length of the ligament graft 30 will be evidenced by a change in load registered by the load cells 62 while the joint is externally loaded through cable 70. This information can be used for adjusting the attachment site for the femoral end using a device such as shown of FIGS. 7 and 8.

Figure 7:
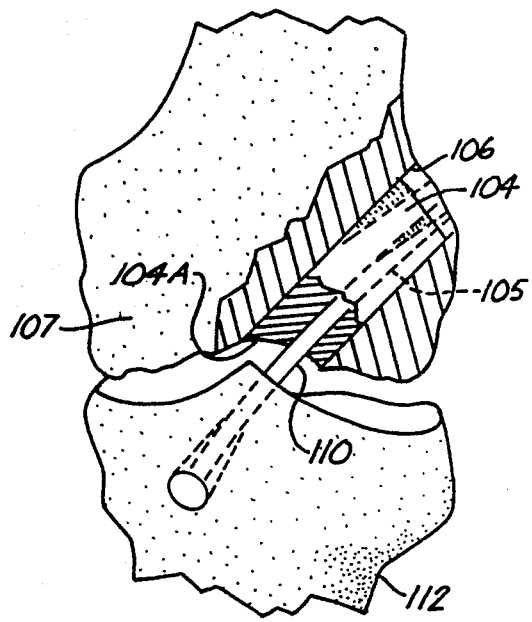
FIG. 7 is an end view of a typical bone plug made to fit a cavity that is bored out with the counter bore device shown in FIG. 5.
Figure 8:
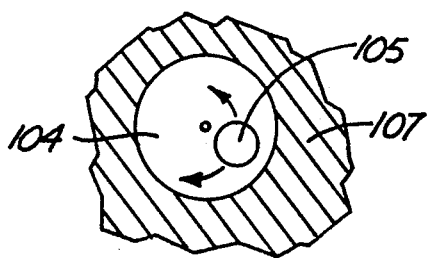
FIG. 8 is a side view of such bone plug of FIG. 7.
Figure 5:
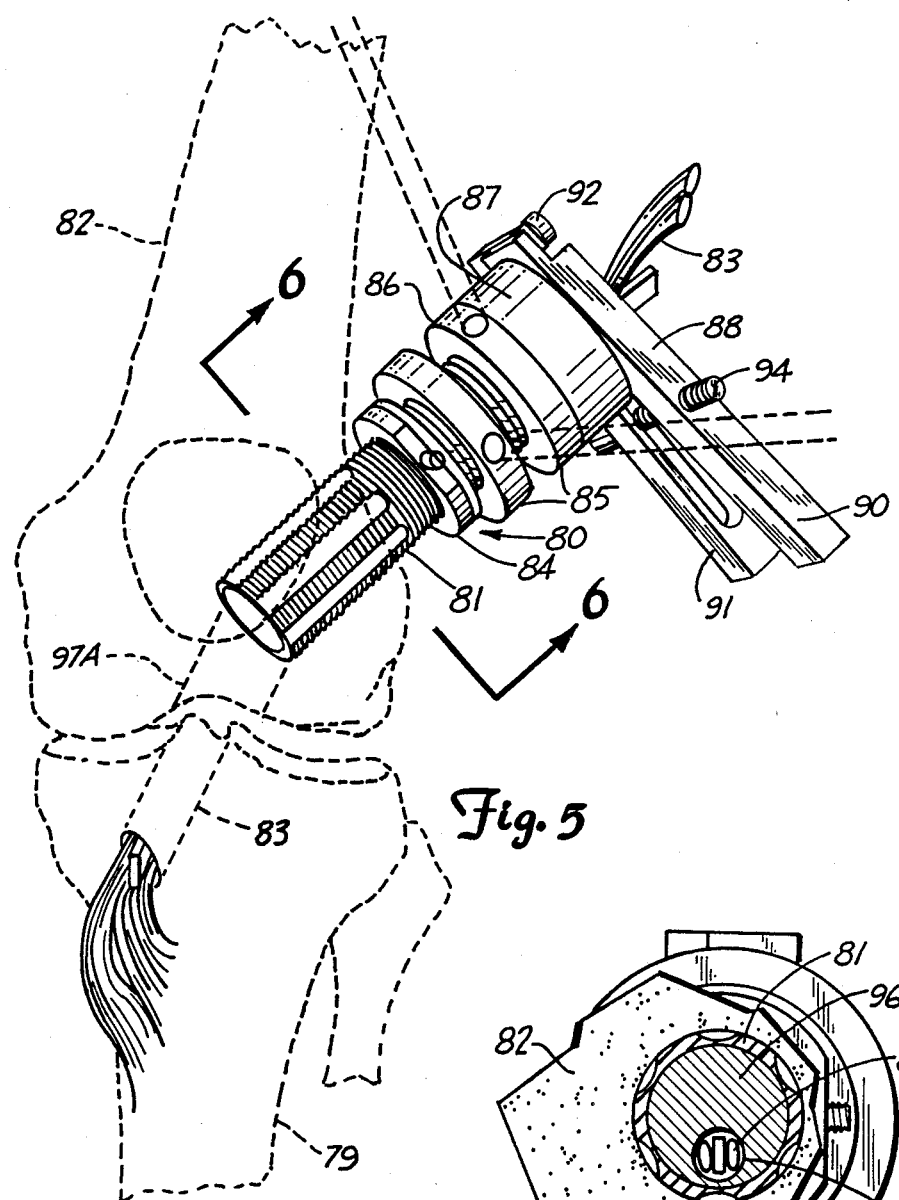
FIG. 5 is a schematic representation of a ligament adjustment device for adjusting the length and attachment position of a ligament in any joint.
Figure 6:
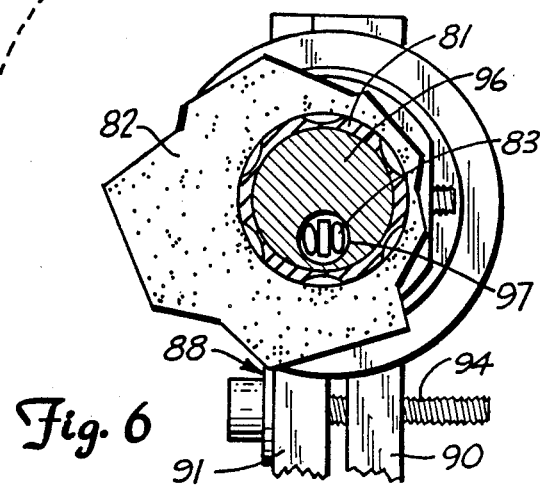
FIG. 6 is a sectional view taken generally along line 6—6 in FIG. 5.

In order to vary the effective ligament graft attachment site location, the device shown in FIGS. 5 and 6 was advanced, leading to the method and device of FIGS. 7 and 8. The device shown in FIGS. 5 and 6 is a prototype device that is not implanted or used in live patients, but permits analysis of the effect of changing the position of the port or opening of the tunnel at the end surface of a femur and tibia model or from a cadaver. The model femur 82 and tibia 79 are shown in dotted lines only, but the attachment site locating device indicated generally at 80 includes an outer threaded casing 81 that forms a housing. The threads 81, as shown, are the type that will self-tap when threaded into a bore existing in the femur 82. The bore can be made initially with a cannulated drill, or the casing 81 may be cannulated and used to make a bore and remove a bone plug, after which the casing 81 is threaded in place. The tunnel size for receiving the threaded portion 81 is large so lateral positions of the ligament graft can be changed. The tunnel is larger than the bundle of ligament graft segments shown generally at 83.

The outer casing 81 has a stop collar 84 that can be used for placing it at a desired location against the outer surface of the joint end of the femur 82, and at the end outwardly from the stop collar 84, there are a pair of threaded collars 85 and 86, which can be rotated to bear against a slidable collar 87 that slidably fits over the end of casing 81 and which carries a ligament graft clamp 88 at the outer end. The ligament graft bundle 83 extends outwardly from the clamp 88 and can be clamped in a scissor-like arrangement. The clamp 88 has a pair of arms 90 and 91, that are pivotally mounted together with a pin 92 adjacent one end, and this pin 92 is attached to the sliding collar 87. With the ligament graft between the arms 90 and 91, a screw 94 can be threaded to tighten the arms 90 and 91 together about the pivot pin 92 and clamp the ligament graft 83 to hold it securely. The collar 86 can be adjusted to push on collar 87 to change the length of the ligament graft before fixing it in place.

The ligament graft 83 passes through a cylindrical hub or plug 96 that is rotatably mounted on the inside of the threaded casing, as shown in FIG. 6. If the casing is used for making its own tunnel, the hub or plug 96 would be removed, and the bone plug formed would also be removed. Hub 96 has a tunnel or bore 97 therein that is offset from the center of rotation of the outer surface of the hub 96, so that upon rotation of the hub 96 the position of the tunnel 97 will change. This will then change the position of the site where the ligament graft exits the interface surface of the femur for the knee joint (or other joint). Changing of the site of the ligaments at the interface surface on the femur and on the tibia, as has previously been explained, can be very critical so that by proper adjustment a good ligament graft can be properly positioned and held in place. The hub 96 can be rotated about its axis, which will displace the tunnel 99 laterally because of its offset from the center of the hub. The site of exit of the ligament graft from the femur can be changed if a large tunnel section such as that shown in 97A is provided. The ligament graft can be secured in a desired location by use of securing means that will hold the graft in a desired lateral position.

In order to have the site of exit of the graft adjustable for a permanent replacement in a living person, a bone plug 104 as shown in FIGS. 7 and 8, can be removed from another bone of the person being treated, and inserted into a tunnel or bore 106 formed to the desired size for the cylindrical bone plug 104. The bone plug 104 has a tunnel 105 offset from the bone plug axis. The tunnel 105 can be shifted laterally by rotating it in tunnel 106 to shift the attachment point of a ligament graft 110 at the femoral interface surface. A fixture of FIGS. 2–4 can be adapted to attach to the femur at the exterior of the tunnel 106 and load a ligament graft 110 secured in a tibia 112 to adjust the length of the ligament graft.

The opening of tunnel 105 can be positioned at a desired location at the interface at the knee joint by rotating the bone plug 104 about its axis, in the same manner that the hub 96 of FIG. 5 is rotated, to change the effective site of attachment of the ligament graft. The bone plug 104 can be rotated about its axis until the port from the tunnel in the bone plug is positioned at a location where knee flexion can occur with minimum change in length of the ligament graft, as indicated by little change in force measured with a fixture having manually adjustable, length adjusting assemblies 50 thereon.

The ligament graft 110 can be fixed to the tunnel 105 as previously shown with a screw, and then the bone plug 104 itself can be secured into the bore 106 in the femur by a lock screw or other suitable means, once the appropriate site of the ligament graft has been selected.

The end surface 104A of bone plug 104 facing the tibia can be shaped to conform to the knee joint end surface shape of the femur after the plug 104 has been rotated to the desired position and secured. It should be noted that a plug such as that shown in 104 can also be used in the tibia, but it would be of smaller diameter. If desired individual tunnels can be bored into such plug for carrying the individual segments of the ligament graft so that the segments all can be adjusted for proper location where they cross the interface surface at the knee or other joint.

The ability to change the effective attachment site with a hub or a plug that has an eccentric tunnel formed in it, and which can be rotated inside a larger tunnel to change the position of the ligament graft where it exits the interface of a joint provides for greater adjustability, and by properly adjusting the ligament graft length and utilizing means for ensuring that individual segments of a ligament graft are adjusted in length to carry selected portions of the total load, a satisfactory reconstruction can be achieved.

The ideal situation is that the ligament grafts are positioned in such a location that they do not change in length to any substantial degree as the knee flexes through its full range of unloaded flexion. The proper length adjustment as indicated by force in the graft segments prior to fixation with the knee under external load provides the proper relationship of the joint parts when the external load on the joint is unloaded.

It should be noted that the ligament segments do not have to extend all the way out to the clamps on the length adjusting assemblies 50, but sutures can be placed onto the ligament graft segments and the sutures clamped in place to provide the length changes. Applying a desired standardized external joint load to the knee, and then adjusting the length of each of the individual ligament graft segments so that the total graft force is as desired, and which may be related to normal forces in the ligament being replaced, means precise control for a good reliable graft can be achieved. By ensuring that the lengths are proper for joint operation before securing the graft, the reconstruction is greatly enhanced.

The load adjusting devices can be used for extra articular grafts wherein tissue or ligament graft material is applied to an external part of the joint. No tunnels are used, but the ligament graft can be adjusted in length easily. The frame 42 would be located to guide the ligament graft to its desired location in the bone segment.

Additional force measuring devices may also be used such as a "buckle" transducer which goes directly onto a ligament having a frame with end cross bars and a center cross bar. The ligament graft is threaded under the end bars of the buckle frame and over the center cross bar, so that when the ligament tends to straighten out it will exert loads on both end bars and the cross bar. Strain gauges are used on such buckle to sense loads.

The external load applied through the cable 70 can be done with a strain gauge force ring, or any desired load indicating device.

Although the present invention has been described with reference to preferred embodiments, workers skilled in the art will recognize that changes may be made in form and detail without departing from the spirit and scope of the invention.

What is claimed is:

1. A method of replacing ligaments in a joint of a human body between first and second bone portions comprising the steps of:
   temporarily fixing a replacement ligament graft at a first attachment site relative to a first of said bone portions, in a provided tunnel;
   passing the replacement ligament graft into a tunnel in a second bone portion;
   changing the location where the replacement ligament graft exits the tunnel in the first bone portion while measuring length changes of the replacement ligament graft as reflected by total forces in the replacement ligament graft while under external load; and
   fixing the replacement ligament graft to the second bone portion at a second attachment site and fixing the location where the replacement ligament graft exits the tunnel in the first bone portion to minimize changes in length of such replacement ligament graft during a desired amount of flexion of the joint.

2. The method of claim 1 including the further step of applying a load on the replacement ligament graft to a desired level prior to fixation of the replacement ligament graft to the second bone portion.

3. The method of claim 1 including the step of varying the length of the replacement ligament graft between the first and second attachment sites on the two bone portions so that force in the replacement ligament graft is substantially matching normal loading of a natural ligament for the joint.

4. The method of claim 1 including the step of using a multi-segment replacement ligament graft and determining the load carried in the individual replacement ligament graft segments as the length thereof is adjusted prior to fixation of the replacement ligament graft segments with the joint under external load.

5. An apparatus for use in installing replacement ligament graft members of either single or multiple segments to a joint between first and second bone components comprising:
   a removable fixture mountable on a first bone component adjacent to a joint in which a ligament graft member is to be used for joining the two bone components;
   the fixture comprising a frame;
   means for removably mounting said frame on the first bone component, said means for removably mounting being separate from any means fixing the ligament graft member to a bone component;
   means on the frame for adjusting the length of a ligament graft relative to the frame with the joint under a prescribed load, said means for adjusting being positionable adjacent a ligament graft member path on the first bone segment; and
   means for coupling the means for adjusting to the ligament graft member whereby the length of the ligament graft member can be adjusted while the joint is under load prior to fixation of the ligament graft member to both bone components.

6. The apparatus of claim 5 including force measuring means coupled to the means for adjusting to determine the tension in a ligament graft member as the length of such ligament graft is adjusted.

7. The apparatus as specified in claim 6 wherein said frame includes a load carrying member independent of the means for adjusting for permitting exerting an external load to the joint before the length of the ligament graft member is adjusted.

8. The apparatus of claim 5, said length adjusting means including a clamp for receiving a ligament graft member, and a screw threadable for moving the clamp to change the length of the ligament graft member.

9. The apparatus of claim 8 and guide pulley means for guiding a ligament graft member for aligning such ligament graft member with the clamp.

10. The apparatus of claim 9 and a load cell carrying forces from the screw to the clamp to measure loads carried on the ligament graft member.

11. An apparatus for providing a guide for locating a ligament graft member relative to a first bone segment adjacent to a joint with a second bone segment for which said joint ligament graft member is to be used, said apparatus comprising:
   means for providing a first tunnel in the first bone segment through which a graft will extend; and
   plug means for mounting in said first tunnel comprising a plug having a central axis and a second tunnel through the plug extending substantially parallel to the central axis, the second tunnel being offset form the central axis, said second tunnel receiving a ligament graft member, and said plug being rotatable about its central axis to change the exit position of the ligament graft member received in the second tunnel in respect to a tunnel formed in a second bone segment forming the joint.

12. The apparatus specified in claim 11 and means to clamp a ligament graft member passing through said second tunnel of said plug, and means to move the clamp to adjust the length of a ligament graft held therein when the opposite end of such a ligament graft member is retained in the second bone segment against movement.

13. The apparatus of claim 11 and means for securing the plug with the second tunnel in a selected rotational position about its central axis.

14. An apparatus for use in installing ligament graft members to a joint between first and second bone components, said ligament graft member comprising a plurality of individual, elongated graft segments which share load carried by the graft member comprising:
a fixture mountable on a first bone component adjacent to as joint in which a ligament graft member is to be used for joining the two bone components;
the fixture comprising a frame;
means for mounting said frame on the first bone component;
a plurality of individual adjustable members on the frame for individually adjusting the length of each graft segment relative to the frame with the joint under a prescribed load, said adjustable members being positionable adjacent a ligament graft member path on the first bone segment; and
means for coupling the individual adjustable members to the respective individual graft segments.

15. An apparatus for use in installing ligament graft members of either single or multiple segments to a joint between first and second bone components comprising:
a fixture mountable on a first bone component adjacent to a joint in which a ligament graft member is to be used for joining the two bone components;
the fixture comprising a frame;
means for mounting said frame on the first bone component;
means for adjusting the length of a ligament graft member relative to the frame with the joint under a prescribed load, said means for adjusting comprising a clamp for receiving a ligament graft member and being positionable adjacent a ligament graft member path on the first bone segment and force generating means for moving the clamp relative to the frame; and
a load cell carrying forces from the force generating means to the clamp to measure loads carried through the ligament graft member.

* * * * *

UNITED STATES PATENT AND TRADEMARK OFFICE
CERTIFICATE OF CORRECTION

PATENT NO. : 4,950,271

DATED : August 21, 1990

INVENTOR(S) : Jack L. Lewis et al.

It is certified that error appears in the above-identified patent and that said Letters Patent is hereby corrected as shown below:

```
        Col. 10, line 52, delete "claim 9, insert
--claim 8--.
        Col. 10, line 65, delete "form", insert
--from--.
        Col. 11, line 20, delete "as", insert --a--.
```

Signed and Sealed this

Seventh Day of January, 1992

*Attest:*

HARRY F. MANBECK, JR.

*Attesting Officer*        *Commissioner of Patents and Trademarks*